US008802408B2

(12) United States Patent
Fieldhouse et al.

(10) Patent No.: US 8,802,408 B2
(45) Date of Patent: Aug. 12, 2014

(54) PROCESS FOR PREPARING NUTRITIONAL, THERAPEUTIC OR ORGANOLEPTIC PRODUCTS FROM CRUDE GLYCEROL

(75) Inventors: Robin Fieldhouse, Kingston (AU); Donald Finlay MacLennan, Borenore (AU); David Graham MacLennan, Killcare (AU); Mary Elizabeth MacLennan, Killcare (AU)

(73) Assignee: Bio Processing Australia Pty Ltd. (AU)

( * ) Notice: Subject to any disclaimer, the term of this patent is extended or adjusted under 35 U.S.C. 154(b) by 734 days.

(21) Appl. No.: 12/863,152

(22) PCT Filed: Jan. 16, 2009

(86) PCT No.: PCT/AU2009/000053
§ 371 (c)(1),
(2), (4) Date: Sep. 23, 2010

(87) PCT Pub. No.: WO2009/089593
PCT Pub. Date: Jul. 23, 2009

(65) Prior Publication Data
US 2011/0044972 A1 Feb. 24, 2011

(30) Foreign Application Priority Data

Jan. 18, 2008 (AU) ................................ 2008900238
Jan. 31, 2008 (AU) ................................ 2008900396
Jul. 24, 2008 (AU) ................................ 2008903778

(51) Int. Cl.
*C12N 1/20* (2006.01)
*C12N 1/16* (2006.01)
*A61K 36/06* (2006.01)
*C12P 1/02* (2006.01)

(52) U.S. Cl.
USPC ...................... 435/171; 435/253.6; 435/255.1; 424/115; 426/62

(58) Field of Classification Search
None
See application file for complete search history.

(56) References Cited

U.S. PATENT DOCUMENTS

| 4,322,498 A * | 3/1982 | Takayama et al. ......... 435/255.4 |
| 4,530,846 A | 7/1985 | Nagodawithana et al. |
| 6,902,912 B2 * | 6/2005 | Benedetti et al. ............ 435/71.1 |
| 2003/0119109 A1 * | 6/2003 | van den Burg et al. ...... 435/69.1 |
| 2005/0089530 A1 | 4/2005 | Moesgaard et al. |
| 2008/0227179 A1 * | 9/2008 | Smith et al. ................ 435/255.1 |
| 2010/0028965 A1 | 2/2010 | Liu et al. |

FOREIGN PATENT DOCUMENTS

| CA | 1014498 | 7/1977 |
| EP | 1 693 447 A1 | 8/2006 |
| EP | 1 892 300 A1 | 2/2008 |
| GB | 1 319 114 A | 6/1973 |
| GB | 1 449 534 | 9/1976 |
| GB | 2 091 285 A | 7/1982 |
| WO | 03/078605 A1 | 9/2003 |
| WO | 2009/143007 A2 | 11/2009 |

OTHER PUBLICATIONS

Yoon, J.J. (2011) What's the Difference Between Biodiesel and Renewable (Green) Diesel. Advanced Biofuels USA pp. 1-14.*
Bain, R. (2006) Biodiesel and Other Renewable Diesel Fuels. National Renewable Energy Laboratory pp. 1-2.*
Agri-Growth International, Inc., "Equine Chromium Selenium Yeast," accessed on Nov. 21, 2008 from <http://www.agriorganics.com/horsecare/minerals.html>, 4 Pages.
Asad-Ur-Rehman, et al., "Pre-Treatment and Utilization of Raw Glycerol from Sunflower Oil Biodiesel for Growth and 1,3-propanediol Production by Clostridium Butyricum," Journal of Chemical Technology and Biotechnology, 2008, pp. 1072-1080, vol. 83, No. 7.
Ashby, R., et al., "New Uses for Glycerol: Fermentation Substrates for Value-Added Product Synthesis," Abstract, Annual Meeting and Expo of the American Oil Chemists' Society, Apr. 30, 2006, p. 72.
Celik, E., et al., "Use of Biodiesel Byproduct Crude Glycerol as the Carbon Source for Fermentation Processes by Recombinant Pichia Pastoris," Industrial Engineering and Chemistry Research, 2008, pp. 2985-2990, vol. 47, No. 9.
Chen, H.-C., et al., "Production of y-Linolenic Acid by the Fungus Cunninghamella Echinulata CCRC 31840," Biotechnology Progress, 1996, pp. 338-341, vol. 12, No. 3.
Da Silva, G. P., et al., "Glycerol: A Promising and Abundant Carbon Source for Industrial Microbiology," Biotechnology Advances, 2009, pp. 30-39, vol. 27.
Himmi, E. H., et al., "Nutrient Requirements for Glycerol Conversion to 1,3-propanediol by Clostridium Butyricum," Bioresource Technology, 1999, pp. 123-128, vol. 67, No. 2.
Imandi, S. B., et al., "Optimization of Medium Constituents for the Production of Citric Acid from Byproduct Glycerol Using Doehlert Experimental Design," Enzyme and Microbial Technology, 2007, pp. 1367-1372, vol. 40.
Ito, T., et al., "Hydrogen and Ethanol Production from Glycerol-Containing Wastes Discharged after Biodiesel Manufacturing Process," Journal of Bioscience and Bioengineering, 2005, pp. 260-265, vol. 100, No. 3.
Kocsisova, T., et al., "G-Phase from Methyl Ester Production—Splitting and Refining," Petroleum & Coal, 2006, pp. 1-5, vol. 48, No. 2.

(Continued)

*Primary Examiner* — Lisa J Hobbs
(74) *Attorney, Agent, or Firm* — Senniger Powers LLP

(57) ABSTRACT

The present invention relates to a process for preparing a nutritional, therapeutic or organoleptic product by growing non-recombinant yeast under aerobic conditions, in a medium that includes crude glycerol, as one possible carbon source to produce a yeast product. The yeast product can be processed to obtain such nutritional, therapeutic or organoleptic products as yeast paste, yeast metabolites, carbohydrates, proteins, functional proteins, nucleotides, yeast autolysates, yeast extract, yeast cell walls, beta-glucans, mannans or a product derived from a mineralized yeast product.

23 Claims, No Drawings

(56) References Cited

OTHER PUBLICATIONS

Mantzouridou, F., et al., "Industrial Glycerol as a Supplementary Carbon Source in the Production of Beta—Carotene by Blakeslea Trispora," Journal of Agricultural and Food Chemistry, 2008, pp. 2668-2675, vol. 56, No. 8.

Meesters, P. A. E. P., et al., "High-Cell-Density Cultivation of the Lipid Accumulating Yeast Cryptococcus Curvatus Using Glycerol as a Carbon Source," Applied Microbiology and Biotechnology, 1996, pp. 575-579, vol. 45.

Merck, Glycerol 85% Specification Sheet, printed Jan. 12, 2009, 2 Pages.

Moraes, D. A., et al., "Influence of the Initial Glycerol Concentration on the Specific Growth Rate of Candida Utilis Cultivated on a Synthetic Medium Containing Glycerol as the Main Carbon Source," Biotechnology Letters, Aug. 1996, pp. 943-946, vol. 18, No. 8.

Ooi, T. L., et al., "Crude Glycerine Recovery From Glycerol Residue Waste from a Palm Kernel Oil Methyl Ester Plant," Journal of Oil Palm Research, Dec. 2001, pp. 16-22, vol. 13, No. 2.

Papanikolaou, S., et al., "Biotechnological Valorisation of Raw Glycerol Discharged after Bio-Diesel (Fatty Acid Methyl Esters) Manufacturing Process: Production of 1,3-propanediol, Citric Acid and Single Cell Oil," Biomass and Bioenergy, 2008, pp. 60-71, vol. 32.

Papanikolaou, S., et al., "Lipid Production by Yarrowia Lipolytica Growing on Industrial Glycerol in a Single-Stage Continuous Culture," Bioresource Technology, 2002, pp. 43-49, vol. 82.

Papanikolaou, S., et al., "Modelling Aspects of the Biotechnological Valorization of Raw Glycerol: Production of Citric Acid by Yarrowia Lipolytica and 1,3-propanediol by Clostridium Butyricum," Journal of Chemical Technology and Biotechnology, 2003, pp. 542-547, vol. 78, No. 2.

Papanikolaou, S., et al., "Yarrowia Lipolytica as a Potential Producer of Citric Acid from Raw Glycerol," Journal of Applied Microbiology, 2002, pp. 737-744, vol. 92.

Pollock, C., "Biodiesel Byproduct May be Used as Value-Added Ag Commodity," accessed on Dec. 15, 2008 from <http://extension.osu.edu/~news/story.php?id=4912>, 2 Pages.

Pyle, D. J., et al., "Producing Docosahexaenoic Acid (DHA)-Rich Algea from Biodiesel-Derived Crude Glycerol: Effects of Impurities on DHA Production and Algal Biomass Composition," Journal of Agricultural and Food Chemistry, 2008, pp. 3933-3939, vol. 56, No. 11.

Pyle, D. J., "Use of Biodiesel-Derived Crude Glycerol for the Production of Omega-3 Polyunsaturated Fatty Acids by the Microalga Schizochytrium Limacinum," A Thesis submitted to the Faculty of Virginia Polytechnic Institute and State University, Apr. 18, 2008, 83 Pages.

Rymowicz, W., et al., "Citric Acid Production from Raw Glycerol by Acetate Mutants of Yarrowia Lipolytica," Chemical Papers, 2006, pp. 391-394, vol. 60, No. 5.

Rymowicz, W., "New Uses for Glycerin from Bio-Rafineries," accessed on Nov. 24, 2008 from <http://www.kpk.gov.pl/pliki/9233/Waldemar%20Rymowicz%20glycerol.pdf>, 7 Pages.

Tang, S., et al., "Pichia Pastoris Fermentation for Phytase Production Using Crude Glycerol From Biodiesel Production as the Sole Carbon Source," Biochemical Engineering Journal, 2009, pp. 157-162, vol. 43.

Thompson, J. C., et al., "Characterization of Crude Glycerol from Biodiesel Production from Multiple Feedstocks," Applied Engineering in Agriculture, 2006, pp. 261-265, vol. 22, No. 2.

Triboli, E. P. D. R., et al., "Influence of the Temperature on Batch Cultivation of Candida Utilis IZ-1840 on a Synthetic Medium Containing Glycerol as the Main Carbon Source," Biotechnology Letters, Apr. 1994, pp. 385-388, vol. 16, No. 4.

Chi, Z., et al., "A Laboratory Study of Producing Docosahexaenoic Acid from Biodiesel-Waste Glycerol by Microalgal Fermentation," Process Biochemistry, 2007, pp. 1537-1545, vol. 42, No. 11.

Rymowicz, W., et al., "Biosynthesis of Citric Acid from Crude Glycerol by Yarrowia lipolytica in Repeated-Batch Cultivations," Abstracts, Journal of Biotechnology, 2007, pp. S149-S150, vol. 131S, No. 2.

Rymowicz, W., et al., "High-Yield Production of Erythritol from Raw Glycerol in Fed-Batch Cultures of Yarrowia lipolytica," Biotechnology Letters, Nov. 27, 2008, pp. 377-380, vol. 31, No. 3.

Athalye, S. K., et al., "Use of Biodiesel-Derived Crude Glycerol for Producing Eicosapentaenoic Acid (EPA) by the Fungus Pythium irregulare," Journal of Agricultural and Food Chemistry, 2009, pp. 2739-2744, vol. 57, No. 7.

\* cited by examiner

PROCESS FOR PREPARING NUTRITIONAL, THERAPEUTIC OR ORGANOLEPTIC PRODUCTS FROM CRUDE GLYCEROL

FIELD OF THE INVENTION

The present invention relates in particular, but not exclusively, to a process for the production of nutritional, therapeutic and/or organoleptic products by fermentation of yeast using crude glycerol as a feedstock.

BACKGROUND OF THE INVENTION

Crude glycerol is available in bulk quantities as a by-product of such processes as soap and detergent manufacture, alcoholic beverage manufacture, fatty acid production and biodiesel manufacture. Biodiesel is a vegetable oil or animal fat derived fuel that can be used in diesel engines and heating systems. The fuel is renewable, non-toxic and its use results in lower harmful emissions. Consequently, biodiesel production worldwide has surged as an attractive alternative to expensive and polluting petroleum-based fuels. In 2008, the United States National Biodiesel Board reported that the production of biodiesel in the United States alone reached 2.24 billion gallons per year (see http://www.biodiesel.org/pdf files/fuelfactsheets/production capacity.pdf). With such large amounts of biodiesel being produced, the excess crude glycerol is superseding the demand for glycerol in such conventional applications as cosmetics, personal care products and pharmaceuticals. Further, the expensive and energy-intensive process of refining the crude glycerol for such uses precludes refinement as the complete solution for the excess glycerol.

There are various processes being evaluated to deal with the oversupply of crude glycerol including using the crude glycerol as animal feed (see for example, Cerrate et al. (2006) Int. J. Poult. Sci. 5:1001) and converting the crude glycerol into products such as 1,3-propanediol (see for example, Asad-ur-Rehamn et al. (2008) Journal of Chemical Technology & Biotechnology, 83(7):1072). However, the viability of these processes on a commercial scale may prove difficult to achieve and consequently, there remains a need for viable processes to convert the excess glycerol into high value products.

SUMMARY OF THE INVENTION

The present invention provides a process for the utilization of crude glycerol to produce a nutritional, therapeutic or organoleptic product of high quality and value.

According to a first embodiment of the present invention there is provided a process for preparing a nutritional, therapeutic or organoleptic product comprising:
  (a) growing non-recombinant yeast, under aerobic conditions, in the presence of a medium comprising crude glycerol, as at least one carbon source, and one or more sources of nitrogen to produce a yeast product; wherein the carbon to nitrogen ratio of the medium is less than 90:1; and
  (b) processing the yeast product to obtain the nutritional, therapeutic or organoleptic product.

According to a second embodiment of the present invention there is provided a process for preparing a nutritional, therapeutic or organoleptic product comprising:
  (a) growing *Candida utilis* under aerobic conditions, in the presence of a medium comprising crude glycerol, as at least one carbon source, and one or more sources of nitrogen to produce a yeast product; and
  (b) processing the yeast product to obtain the nutritional, therapeutic or organoleptic product.

According to a third embodiment of the present invention there is provided a process for preparing a nutritional, therapeutic or organoleptic product comprising:
  (a) growing non-recombinant yeast under aerobic conditions, in the presence of a medium comprising crude glycerol, as at least one carbon source, one or more sources of nitrogen and one or more elements selected from the group consisting of selenium, chromium, molybdenum, germanium, zinc, iron, copper, magnesium, manganese, iodine and combinations thereof to produce a mineralized yeast product; and
  (b) processing the mineralized yeast product to obtain the nutritional, therapeutic or organoleptic product.

According to a fourth embodiment of the present invention there is provided a nutritional or organoleptic product that is suitable for human and/or animal use and that is prepared by the process described in the first, second or third embodiment of the present invention.

According to a fifth embodiment of the present invention there is provided a therapeutic product that is suitable for human and/or animal use and that is prepared by the process described in the first, second or third embodiment of the present invention.

DETAILED DESCRIPTION OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Documents referred to within this specification are included herein in their entirety by way of reference.

The reference to any prior art in this specification is not, and should not be taken as, an acknowledgment or any form of suggestion that that prior art forms part of the common general knowledge in Australia.

As mentioned above, in one broad embodiment this invention relates to a process for preparing a nutritional, therapeutic or organoleptic product that is derived from yeast by growing the yeast on a medium that includes crude glycerol. The yeasts that can be grown according to the process of the present invention are non-recombinant yeast organisms that are capable of using crude glycerol as a source of assimilable carbon. By the term "non-recombinant yeast", it is intended to mean a yeast organism in which the genome has not been deliberately altered by either the introduction of genetic material from another organism or the removal of genetic material. Therefore, yeast organisms that are suitable for the present invention can include organisms in which the genome has been randomly altered, without inserting foreign genetic material therein, by such genetic engineering techniques as, but not limited to, selective breeding and/or mutation under selective pressure.

Such non-recombinant yeast organisms include, but are not limited to, *Candida utilis, Candida curvata, Candida hispaniensis, Candida bentonensis, Kluyveromyces marxianus, Saccharomyces bayanus, Saccharomyces cerevisiae* or a combination thereof. Preferably, the yeast is *Candida utilis*. It may also be desirable to grow, in accordance with the present invention, two or more yeast organisms to produce a combined yeast biomass.

Other examples of yeast organisms may include but are not limited to those yeast species or strains thereof that belong to the following genera: *Torulopsis, Rhodotorula, Kluyveromyces, Debaromyces, Pichia, Geotrichum, Hansenulae, Cellulomonas, Trichosporon, Xanthomonas, Yarrowia, Aciculoconidium, Cryptococcus, Apiotrichum, Mortierella, Cunninghamellae, Mucorales, Mucor, Rhizopus* or *Basidiomycetes* and that are non-recombinant and capable of using crude glycerol as a carbon source. As appreciated by those skilled in the art, each of the yeast organisms listed above may have alternate classifications. For example, *Candida utilis* is also known as *Pichia jadinii*.

By the term "crude glycerol", it is intended to mean glycerol that has been produced by one or more processes, including but not limited to, transesterification of plant oils or animal fats in order to produce biodiesel, hydrolysis of fats or oils to produce fatty acids and saponification of fats or oils to produce soap and detergents and that has not been distilled. Crude glycerol obtained from such processes can have a range of impurity levels.

As a by-product of the biodiesel process, for example, the crude glycerol may contain approximately from 15% to approximately 95% glycerol on a weight by weight basis (wt/wt), as well as varying amounts of impurities that include, but are not limited to, fatty acids and/or salts thereof, short chain alkyl alcohols such as methanol or ethanol, inorganic salts, water and MONG (Matter Organic Non-Glycerol) including mono- and di-glycerides, diglycerol, polyglycerol ethers, acrolein (if, for example, high temperature cooking oil is the biodiesel feedstock) and biodiesel itself. The pH of crude glycerol obtained from biodiesel production can range approximately from 2 to 12 and more often from approximately 4 to 10. Such variations in the pH, the nature of impurities and the amount of each impurity in the crude glycerol arises from a range of factors, including the quality and purity of the biodiesel feedstock (triglycerides), amount of catalyst used in the transesterification process and the processing technology employed. For example, crude glycerol obtained from biodiesel production can contain from 60 to 85% wt/wt of glycerol with the balance being fatty acids or salts thereof (5-35% wt/wt), inorganic salts (5-20% wt/wt) and MONG (<10% wt/wt).

It is preferred that the crude glycerol used in accordance with the present invention contains approximately from 20 to approximately 95% wt/wt glycerol. More preferably, the crude glycerol contains approximately from 40% to approximately 90% wt/wt glycerol. Most preferably, the crude glycerol contains approximately from 80 to approximately 90% wt/wt glycerol.

The impurities present in the crude glycerol, such as fatty acids, methanol, inorganic salts and acrolein may be inhibitory to the growth of certain microorganisms. Such impurities may even be toxic, or simply limit the cell density and/or process productivity achievable. The impurities may also modify the colour, aroma and flavour of the crude glycerol which in turn may affect the colour, aroma and flavour of the yeast products prepared by the process of the invention. For example, the colour of crude glycerol obtained from biodiesel production can be dark brown and depending on the product, such colour may not be acceptable. It is a key aspect of this invention that the colour, aroma and flavour of the resulting yeast derived products are of market-acceptable quality and consistent across a range of crude glycerol quality. Therefore, treatment of the crude glycerol in order to at least partially purify the crude glycerol may be necessary to remove one or more impurities before being added to the culture medium. Alternatively, non-recombinant micro-organisms may be selected which are not inhibited by the impurities, but are still able to provide high-value products or extracts that can be used, for example, for nutritional or medicinal purposes.

In order to effect partial purification of the crude glycerol, the crude material can undergo one or more treatment, including, but not limited to, acidification, absorption and filtration depending on the purity of the crude glycerol and the desired purification to be effected. For example, addition of one or more mineral acids such as phosphoric acid, sulfuric acid, hydrochloric acid or nitric acid, and/or one or more organic acids such as acetic acid, chloroacetic acid, methanesulfonic acid, and analogues thereof, to decrease the pH may cause separation of fatty acids from the crude glycerol, allowing their removal by decanting, centrifugation or other means. If the crude glycerol undergoes acidification, it is preferred that phosphoric acid is used. Removal of volatiles within the crude glycerol such as methanol can be achieved by distillation or other methods if necessary. Mono- and di-glycerides may be removed by, for example, by saponification to additional glycerol and salts of fatty acids. Other possible treatment methods of the crude glycerol include, but are not restricted to, removal of inorganic or organic salts by ion-exchange methods, reverse osmosis, nanofiltration, ultrafiltration and/or filtration through an adsorbent. For example, adverse colours, flavours and aromas may be removed by subjecting the crude glycerol to an adsorbant such as activated charcoal and/or bentonite.

Where more than one purification method is used, any order may be selected, preferably that which most efficiently achieves the desired purification. If the crude glycerol does undergo one or more partial purification steps, it is intended that the content of glycerol in the treated crude glycerol will remain within the approximate range of from 20 to 95% on a weight per weight percentage basis. Further details on the sources of, quality ranges of, and treatment options for, crude glycerol can be found in a number of references, including Glycerine: A Key Cosmetic Ingredient, edited by Eric Jungermannn & Norman O. V. Sonntag, Marcel Dekker Incorporated, 1991, ISBN 978-0824784652 which is incorporated herein by reference. Depending on the quality of the crude glycerol obtained, however, the partial purification step may be omitted.

The process in accordance with the present invention can include the steps of: optionally carrying out a partial purification of the crude glycerol in order to remove or reduce one or more impurities; supplying the treated crude glycerol to an aerobic yeast fermentation system; cultivation of the yeast in batch, fed-batch, semi-continuous, continuous mode or a combination thereof under substantially aseptic conditions; harvesting of the culture and separation of the yeast and recovering and further processing the yeast products of the fermentation. Preferably, the present invention provides a process for producing yeast and yeast-derived products from treated crude glycerol by growing non-recombinant yeast under a continuous and substantially aseptic aerobic fermentation system.

In accordance with the present invention, the treated or untreated crude glycerol within the synthetic medium is one possible source of assimilable carbon for the yeast that can be grown on the synthetic medium. Other sources of assimilable carbon that can be included in the medium together with the untreated or treated crude glycerol include, but are not limited to, such sugars as glucose, fructose, xylose, lactose, maltose, trehalose, sucrose, cellobiose, arabinose and/or galactose as well as sources of fermentable sugars, including but not limited to, brewery sugar residues, molasses, corn steep liquor, wood processing effluent and/or whey. Preferably, the non-recombinant yeasts are grown on a synthetic medium that includes treated or untreated crude glycerol as the sole source of assimilable carbon. Such yeasts include selected strains of *Candida utilis, Saccharomyces cerevisiae, Saccharomyces bayanus* and/or *Kluyveromyces mandanus*. Such yeasts may be further processed to provide human food grade products.

The inoculum, or seed culture, may be prepared as known by those skilled in the art in one mode of operation (batch, fed-batch, semi-continuous, continuous or a combination thereof), then used to charge a fermenter to be operated in the same or a different mode or combination thereof. Details of each mode are known to those skilled in the art and can be, for example, found in the following text: Fermentation and Biochemical Engineering Handbook: Principles, Process Design and Equipment, 2nd Edition, Edited by H C Vogel & C L Todaro, Noyes Publications (New Jersey) 1997, ISBN 0-8155-1407-7 which is incorporated herein by reference. For the purposes of achieving high productivity, a fed-batch, semi-continuous or continuous mode of operation is preferred. Most preferably, the fermenter is operated in continuous mode under substantially aseptic conditions.

During continuous operation, dilution rate (D) is an important parameter as it is the fermenter volume throughput in fermenter volumes per hr, i.e. if D is 0.1 $h^{-1}$, then 200 L of a 2000 L fermenter is being replaced each hour. The optimal dilution rate for an industrial fermenter is determined by the desired productivity, the capacity of downstream processing facilities and the precise details of the product quality required. The maximum growth rate of the organism represents an upper limit on the dilution rate, in order to avoid a "wash out" effect, wherein the cell density in the fermenter decreases rapidly to zero. Preferred dilution rates can be approximately from 0.05 to approximately 0.25 $h^{-1}$. As will be appreciated by those skilled in the art, higher dilution rates may increase the ribonucleic acid content of the biomass produced, which may or may not be desired depending on the application.

In addition to dilution rates, other conditions of the fermentation, such as dissolved oxygen concentration (aeration), nutrient composition, pH and temperature are preferably controlled using conventional means to provide optimum production of yeast. To achieve and sustain high fermentation productivity, it is evident that all nutrients should be available in sufficient quantities or rates.

In particular, the aeration or Dissolved Oxygen (DO) needs to be maintained at levels greater than zero. As known to those skilled in the art, this can be achieved by supplying a large quantity of air to the fermenter together with a high shear mixer. Alternatively, oxygen-enriched air can be supplied to the fermenter. Typical throughputs of gas through the fermenter are in the approximate range of 0.1-10 fermenter volumes per minute (vvm). The precise gas throughput required in order to maintain a DO greater than zero will be dependent on the culture cell density, its specific oxygen uptake requirements, the dilution rate (if applicable), the operating pressure and the physical parameters of the fermenter vessel, amongst other factors. Preferably, the concentration of dissolved oxygen is more than 2% of air saturation, more preferably more than 5% of air saturation.

The concentration of glycerol in the fermentation medium, whether it be provided from untreated or treated crude glycerol, should be sufficient to support further yeast growth and productivity, whilst being below limits which may inhibit yeast growth due to osmotic pressure influences. Preferably, the concentration of glycerol in the medium is approximately from 0.1 g/L to approximately 500.0 g/L. More preferably, the concentration of glycerol in the medium is approximately from 50.0 g/L to approximately 200.0 g/L. Most preferably, the concentration of glycerol in the medium is approximately from 70.0 g/L to approximately 150.0 g/L. A concentration of approximately 70.0 g/L to approximately 150.0 g/L of glycerol in the medium can result in cell densities in the approximate range of 25.0-90.0 g/L on a dry basis. If the medium contains other sources of assimilable carbon in addition to glycerol, then the preferred total concentration of all the carbon sources is approximately from 0.1 g/L to approximately 500.0 g/L. As will be appreciated by those skilled in the art, the concentration of carbon sources in the fermenter may not be the same as the concentration of carbon sources supplied to the fermenter.

Nitrogen is also included in the medium and one or more sources of nitrogen can include, but are not limited to, ammonia, one or more inorganic salts thereof, one or more organic ammonium salts, yeast extract, urea, nitric acid, one or more inorganic nitrite salts and/or one or more inorganic nitrate salts. Preferably, the source of nitrogen in the fermentation medium is ammonia, in aqueous or gaseous form, or one or more inorganic ammonium salts. The ammonia may also be used for pH control during fermentation.

The ratio of carbon to nitrogen (C/N) of the fermentation medium is less than 90:1. Preferably, the C/N ratio is less than or equal to 80:1. More preferably, the C/N ratio is less than or equal to 40:1 and even more preferably, less than or equal to 20:1. Most preferably, the C/N ratio is less than or equal to 10:1. A C/N ratio of 10:1 can result in a yield of 50% of dry biomass from glycerol (on a pure basis). High yields of biomass can be achieved in accordance with the present invention, even though a C/N ratio of less than 90:1 could be expected to result in the yeast having greater exposure to the potentially inhibitory impurities in the untreated or treated crude glycerol.

The lower the carbon to nitrogen ratio is, the more likely that the growth of the yeast will be limited by the amount of carbon available so long as the growth is not limited by other growth limiting factors such as oxygen. In accordance with the present invention, the growth of the yeast can be limited by more than one factor or by a factor other than the available carbon. In the absence of other growth limiting factors, C/N ratios of 90:1 or greater can result in the growth of the yeast being limited by the amount of nitrogen available, whereas C/N ratios of lower than 3:1 can result in inefficient nitrogen utilization.

The medium may also contain one or more macro-nutrients such as mineral salts or elements thereof or micro-nutrients such as vitamins depending on the yeast species or strain thereof. For example, *Candida utilis* requires such elements as S, N, P, K, Mg, Na, Ca, Zn, Fe, Mn, Co, Cu, Mo and B, but does not require vitamins to support growth. If, however, a yeast species or strain thereof requires one or more vitamins such as thiamine, niacin, pyridoxine, biotin, inositol, pantothenic acid and the like, one of skill in the art would recognize that the supply of the vitamin(s) would preferably be independent of other feeds and would also be provided in the requisite amount of vitamin(s) for the particular yeast organism.

The concentration of elements in the medium is determined by a number of factors. The lower concentration limit is determined by the requirements of the particular strain of yeast under the particular growth conditions. The upper concentration limit is determined by the concentration at which a particular element can become inhibitory or even toxic to the growth of the particular species. Inhibition/toxicity can be specific to certain elements (for example, heavy metals are essential at low levels, but toxic at high levels), or the effect may be due to ionic strength or osmotic pressure caused by high concentrations.

As will be appreciated by those skilled in the art, the various components of the medium (such as the treated or untreated glycerol, mineral salts or elements thereof, nitrogen source(s), water and optional micronutrients) can be introduced into the fermenter separately, as a single mixture or as two or more separate mixtures, each of which can contain two or more components. Preferably, the mixtures of components that are fed to the fermenter are prepared in a manner that at least reduces, if not eliminates, precipitation.

The pH of the fermenter should be maintained to within those levels satisfactory for the yeast growth, typically from pH 3.0 to 8.0. Preferably, the pH should be maintained at levels at which few other microorganisms are able to grow well, such as less than 4.5, in order to minimise the risk of contamination. Most preferably, the pH should be less than 4.0. The most preferred pH for the growth of *Candida utilis*, for example, in accordance with the present invention has been found by the inventors to be 3.6.

The temperature of the process can also be controlled, and should be high enough that a fast growth rate can be achieved, but within an upper limit determined by the tolerance of the species or strain of yeast. Higher temperatures are preferred where possible. For yeast growth, the temperature can be approximately from 20.0° C. to approximately 40.0° C. More preferably, the temperature can be approximately from 25.0° C. to approximately 36.0° C. The most preferred temperature for the growth of *Candida utilis*, for example, in accordance with the present invention has been found by the inventors to be 35.0° C.

The yield of yeast biomass from the glycerol (whether it is provided from untreated or treated crude glycerol) will be dependent on the yeast species or strain thereof as well as the absence or presence of other potentially limiting factors. Yield is defined as grams of cells (on a dry basis) per gram of carbon source (on a dry basis). In the absence of other limitations, the yield of yeast that is grown in the presence of a medium that contains untreated or treated crude glycerol can be approximately from 25.0% to approximately 80.0%. The corresponding cell density is approximately from 5.0 g/L to greater than or equal to 150.0 g/L on a dry basis. Preferably, the cell density is approximately from 20.0 g/L to greater than or equal to 100.0 g/L on a dry basis. More preferably, the cell density is approximately from 30.0 g/L to greater than or equal to 80.0 g/L on a dry basis. Most preferably, the cell density is greater than 50.0 g/L on a dry basis. Higher cell densities are preferred, in order to minimize water usage and aid in product recovery by dewatering.

Higher cell densities are theoretically achievable, although in continuous mode of operation, the supply of DO may become rate limiting unless the dilution rate is very low. The yield and cell density for *Candida utilis* grown on crude glycerol in a continuous mode in accordance with the present invention has been found by the inventors to be similar, or even better than the yield and cell density achieved with pure glycerol, depending on the purity of the crude glycerol used. It has also been found that the process of the present invention can result in yeast growth that exhibits a process productivity rate that is greater than or equal to $0.85$ $g.L^{-1}.h^{-1}$. Preferably, the process productivity rate is greater than or equal to $1.00$ $g.L^{-1}.h^{-1}$, more preferably, the rate is greater than or equal to $2.00$ $g.L^{-1}.h^{-1}$ and most preferably the rate is greater than or equal to $3.00$ $g.L^{-1}.h^{-1}$.

Naturally, the products of the present invention are non-toxic, in that they can be considered safe for the intended nutritional, therapeutic or organoleptic use. The yeast product produced by the process of the invention may be the organism itself, secreted metabolites or products derived from further processing of the cultivated yeast. Where the yeast product is the yeast organism itself, the yeast may be used for nutritional, therapeutic or organoleptic purposes in humans, animals or both. Further processing may afford such products as yeast autolysates and extracts, which can be used, for example, as savour flavouring ingredients and flavour enhancers. Other products that can be obtained by the process of the invention include nucleotides, such as GMP and IMP, that can be used as flavour enhancers either alone or in a combination that may also include one or more yeast extracts. Protein fractions derived from the yeast that have such desirable functional properties such as emulsification, thickening, fat-binding, and egg-white substitution are also products according to the invention.

Additional products that can be prepared according to the process of the invention include beta-glucans that are derived from the yeast cell wall. Beta-glucans can have favourable organoleptic properties. An organoleptic product, in accordance with the present invention, is a processed yeast product that provides a desirable taste, colour, odour and/or feel, including mouthfeel, to a final product. For example, in the context of a food preparation, suitable organoleptic properties may include a white or an off-white colour, a palatable flavour such as a meaty or savoury flavour and/or a pleasant odour such a non-yeast like aroma.

Beta-glucans with immunostimulatory properties can also, for example, be used as a therapeutic product in accordance with the present invention. A therapeutic product is defined as either a processed yeast product that ameliorates, improves or treats a disease or disorder (e.g. alleviation of one or more symptoms, or halting, reversing or otherwise slowing down the progression of one or more symptoms of the disease or the severity thereof) or a processed yeast product that has a prophylactic effect (e.g. preventing or delaying the onset of the disease, or symptoms thereof, or otherwise diminishing the extent or severity of symptoms before symptoms of the disease or condition are apparent) in a subject in need thereof.

The therapeutic product can be administered to such subjects as plants (e.g. crops, ornamentals) or animals such as aquatic subjects (e.g. fish, shrimp) or mammalian subjects. Mammalian subjects can include, but are not limited to, humans, primates, livestock animals (including but not limited to cows, horses, sheep, pigs and goats), companion animals (including but not limited to dogs, cats, rabbits, guinea pigs), and captive wild animals. Laboratory animals such as rabbits, mice, rats, guinea pigs and hamsters are also contemplated. Preferably, the subject is a mammalian subject.

Suitable dosage amounts and dosing regimens to achieve the therapeutic effect can be determined by the attending physician or veterinarian and may depend on the particular condition being treated, the severity of the condition as well as the general age, health and weight of the subject. For certain applications (such as animal feed or aquaculture), the dose of the therapeutic product may also be determined by a cost benefit analysis. The therapeutic product may be administered in a single dose or a series of doses. While it is possible for the therapeutic product to be administered alone, it can also be presented as a composition, preferably as a pharmaceutical composition, with one or more carriers, diluents, excipients or adjuvants that is compatible with the other ingredients of the composition and not injurious to the subject (see for example, Remington's Pharmaceutical Sciences, 18th Edition, Mack Publishing, 1990, incorporated herein by reference). These include all conventional solvents, dispersion media, fillers, solid carriers, coatings, antifungal and antibacterial agents, dermal penetration agents, surfactants, isotonic and absorption agents and the like. It will be understood that the compositions may also include other supplementary physiologically active agents.

The therapeutic products or compositions thereof can be suitable for oral, rectal, nasal, topical (including dermal, buccal and sublingual), vaginal or parental (including subcutaneous, intramuscular, intravenous and intradermal) administration. The compositions may conveniently be presented in unit dosage form (including as a capsule, sachet, tablet, powder, granule, lozenge, chewing gum, pastille, mouthwash; a solution, suspension or paste in an aqueous or non-aqueous liquid; or as an oil-in-water liquid emulsion or a water-in-oil liquid emulsion, lotion, gel, cream, ointment or foam) and may be prepared by any methods well known in the art of pharmacy.

In addition to therapeutic products, nutritional products can also be obtained by the process of the present invention. A nutritional product, in accordance with the present invention, is a processed yeast product that can provide, supplement or replenish a nutrient required by a living subject (such as a mammalian subject, including humans and animals as recited above, as well as plants including crop and ornamental vegetation, bacteria and fungi) for growth, reproduction, improvement or maintenance of health and other heterotrophic needs as well as to delay, reverse or prevent premature ageing or symptoms thereof (for example, as a cosmeceutical). The nutritional product can also be used to fortify a food, beverage, water or nutrient supplement source (e.g. salt licks) for any living subject either completely or in part. For example, the nutritional value of the processed yeast product in accordance with the present invention may be the protein and amino acid content, the carbohydrate content (such as a source of dietary fibre) and/or the vitamin content.

In accordance with the present invention, the nutritional product can be derived from a mineralized yeast. Mineralized yeast can, for example, be of value as a supplement in human food or animal feed applications where insufficient quantities of essential trace minerals are available from traditional dietary compositions. The mineralized yeast product according to the invention is grown under aerobic and substantially aseptic conditions in an aqueous medium. The medium includes treated or untreated crude glycerol as one possible carbon source and one or more elements that will be absorbed by the yeast to produce mineralized yeast in a batch, fed-batch, semi-continuous or continuous mode or a combination thereof. The mineralized yeast product is preferably produced in a continuous mode.

The range of conditions and parameters under which the mineralized yeast is grown including, aeration, temperature, pH, C/N ratio, nutrient composition and glycerol concentration, are similar to those conditions and parameters as described above, with the exception that the amount and/or presence of one or more elements in the medium may vary. In order to produce a mineralized yeast product, one or more elements that are intended to be absorbed by the yeast will be added to the medium in sufficient quantities. The addition of the desired element(s) may also require a reduction of one or more other elements in the medium if those elements compete with the absorption of the desired element(s). Certain elements may also be inhibitory to yeast growth, and the fermentation process should be carried out in such a way as to minimize adverse effects of the mineral on the fermentation performance whilst maximizing both the yield of incorporation of the desired element(s) in the yeast and the yield of yeast biomass from the crude glycerol. Suitable methods for achieving this include, but are not limited to, providing a medium deficient in elements such as, for example, sulfur, which may compete with the absorption of the desired element(s) such as selenium, and controlling the supply of the desired element(s). One possible method of preparing a medium that is deficient in sulfur is to add nitric acid to the mineral salts to balance the acidity while lowering the amount of sulfuric acid in the mineral salts. In this way, the nitric acid also serves as a source of nitrogen.

Preferred elements incorporated into the yeast are those providing a health or nutritional benefit to humans or animals, for example, and which are not readily biologically available in the inorganic form, including but not limited to selenium, chromium, molybdenum, germanium, zinc, iron, copper, magnesium, manganese, iodine and combinations thereof. Thus, the mineralized yeast product contains an enhanced level of one or more elements such as selenium, chromium, molybdenum, germanium, zinc, iron, copper, magnesium, manganese, iodine and combinations thereof. These elements are naturally present in only trace levels, and the products of the invention derived from mineralized yeast contain significantly enhanced levels. The enhanced levels may be in the range of from approximately 100 to approximately 50000 parts per million (ppm) of each element on a dry basis, depending on the element, the species or strain of yeast and the conditions under which the yeast is grown. Preferably, the desired element(s) of the mineralized yeast product, on a dry basis, should be substantially in an organic form (such as selenomethionine, for example), to maximize its bioavailability. Although the mineralized yeast product can be processed to produce a nutritional product, it is also contemplated that the mineralized yeast product can be processed to produce a therapeutic product or an organoleptic product.

Yeast organisms that are suitable for producing the mineralized yeast product are any non-recombinant organisms that are capable of both using untreated or treated crude glycerol as a carbon source and absorbing the desired element(s). Such yeasts include, but are not limited to, *Candida utilis, Candida curvata, Candida hispaniensis, Candida bentonensis, Kluyveromyces marxianus, Saccharomyces bayanus, Saccharomyces cerevisiae* or a combination thereof. Preferably, the yeast is *Candida utilis (Pichia jadinii)*. It may also be desirable to grow, in accordance with the present invention, two or more yeast organisms to produce a combined mineralized yeast biomass. Other examples of yeast organisms may include, but are not limited to, those yeast species or strains thereof that belong to the following genera: *Torulopsis, Rhodotorula, Kluyveromyces, Debaromyces, Pichia, Geotrichum, Hansenulae, Cellulomonas, Trichosporon, Xanthomonas, Yarrowia, Aciculoconidium, Cryptococcus, Apiotrichum, Mortierella, Cunninghamellae, Mucorales, Mucor, Rhizopus* or *Basidiomycetes* and that are non-recombinant and capable of both using crude glycerol as a carbon source and absorbing the desired mineral(s) supplied.

The nutritional, therapeutic or organoleptic products in accordance with the invention are obtained by processing the mineralized or non-mineralized yeast product. The yeast product can be collected from the fermentation by any of methods known in the art, such as centrifugation, filtration or others. It may be necessary, for example, to separate the mineralized or non-mineralized yeast product from the supernatant by centrifugation and/or filtration. The resulting yeast paste may then be further processed by one or more of the following processes, including but not limited to, washing, extraction, drying (for example, using a rotary drum dryer or spray dryer), autolysis, fractionation or concentration to produce a nutritional, therapeutic or organoleptic product. The resulting supernatant may also be processed to isolate yeast metabolites from the spent medium in order to produce a nutritional, therapeutic or organoleptic product. Alternatively, the supernatant may be aerobically or anaerobically digested and the resulting water may be separated from the resulting sludge and recycled into the aerobic fermentation process.

The yeast paste can be subjected to homogenization, including high pressure homogenization, sonication and/or other lytic methods (such as the use of detergents) in order to obtain proteins/amino acids and carbohydrates as nutritional, therapeutic or organoleptic products. The protein obtained from the yeast paste can optionally be further derivatized to provide functional proteins which can be used as nutritional, therapeutic or organoleptic products. The optionally derivatised functional proteins can be used for example, as emulsifiers, thickeners, fat binders, egg white substitute and ice-cream stabilizers. The use of yeast biomass for preparation of functional proteins and other products such as nucleotides are described in, for example: Use of Yeast Biomass in Food Production, CRC Press, A. Halasz & R Lasztity, 1991, Chapters 5, 8, and Appendix pages 291-300 and references therein which are incorporated herein by reference.

The yeast paste can also undergo enzymatic digestion with such enzymes as a protease to give yeast extract and yeast cell walls which may be separated by centrifugation and/or filtration. The yeast cell wall fraction can be dried, for example, by rotary drum drying or spray drying, and the resulting dried material can undergo particle size reduction by such processes as milling and sieving). Both the dried yeast cell walls and the yeast extract can be used as nutritional, therapeutic or organoleptic products. For example, the dried yeast cell wall powder can be used as a source of complex polysaccharides or for other nutritional or cosmeceutical purposes. It can also be a source, for example, of beta-glucans with immunostimulatory properties.

Yeast cell walls from *Saccharomyces cerevisiae* that have been produced as a byproduct of the yeast extract process and that have been subsequently dried can contain approximately 30% beta-glucan, approximately 30% mannan, approximately 15% protein and approximately 5-10% lipid, in addition to other components such as mannoproteins and chitin. However, the content of each yeast cell wall component can vary depending on the yeast species or strain thereof. For example, yeast cell walls from *Candida utilis,* that have been prepared and dried in accordance with the invention, can contain approximately 10% beta-glucan and approximately 40% protein.

The beta-glucan content of the yeast cell wall fraction can be enhanced by selective removal of other components, according to methods known in the art such as those relating to the hydrolysis and/or enzymatic degradation of *Saccharomyces cerevisiae* cell walls as an example. Removal of specific non-beta-glucan components can be achieved by chemical and/or enzymatic methods, including but not limited to, lipases for removal of lipid, proteases for removal of protein and mannoprotein and chitinases for removal of chitin. The beta-glucan (with or without the removal of other non-beta glucan components of the yeast cell wall) can be used as a nutritional, therapeutic or organoleptic product. Other components of the yeast cell wall may also be nutritional, therapeutic or organoleptic products in accordance with the invention. Mannans, for example can be removed from the yeast cell fraction by extraction with heated water and then used as a nutritional, therapeutic or organoleptic product.

The invention will now be described further, and by way of example only, with reference to the following non-limiting examples.

EXAMPLES

Example 1

Treatment of Crude Glycerol

Crude glycerol obtained as a by-product from biodiesel production was warmed to approximately 25° C. to liquefy the material. The pH of the crude glycerol was approximately 10.0, and the methanol content <1% w/w. The crude glycerol (1000 L) was transferred to a 1300 L stainless steel tank fitted with overhead agitation and a heating/cooling jacket. After warming to 60° C., an 85% w/w solution of phosphoric acid was pumped slowly into the stirred mixture until an end point pH of 4.0 by titration was reached. Additional water (250 L) was added, to maintain formed salts in solution. The mixture was then allowed to settle for two hours, after which time, the lower aqueous glycerol phase (TCG) was separated and stored for use in the fermentation stage. Alternatively, the mixture can be centrifuged to obtain the upper and lower phases which can then be separated. The glycerol content of the TCG phase was approximately 700 g/L. TCG was diluted to a standard concentration of 500 g/L glycerol before further use. The upper phase, consisting mostly of free fatty acids, was removed for storage, analysis and disposal.

The pale amber to dark brown colour of the TCG can be optionally removed by treatment with bentonite and/or activated charcoal. The bentonite and/or activated charcoal is added to TCG (25 g/L), stirred at ambient temperature, then removed by centrifugation. The resulting TCG can be colourless.

The glycerol content of the phases before and after processing were analysed by HPLC with RI detection, to determine the yield.

Input: 1000 L at approximately 50-60% w/w glycerol which approximately contains 500-600 kg of glycerol Output: approximately 1000 L at approximately 50% w/w glycerol which approximately contains 500 kg of glycerol Yield=approximately 95-100% of glycerol obtained in the TCG The glycerol content of the upper phase was found to be approximately <1% w/w.

Example 2

Continuous fermentation of *Candida utilis* in the presence of treated crude glycerol of Example 1

A 2 L laboratory aerobic fermenter was established with facility for control of pH and temperature and foam, as well as for the measurement of dissolved oxygen (DO), the supply of fermentation media and the harvesting of culture in a continuous manner. Oxygen was supplied to the fermenter as required in order to prevent oxygen-limitation of the continuous culture as required.

Media supplied to the fermenter included the following three components:

(1) treated crude glycerol of Example 1 (as the sole carbon source) having a concentration of approximately 500 g/L glycerol and a pH of 4.0, which was provided at a flow rate of 50 mL/h;

(2) a mixture of (i) mineral salts concentrate (containing S, K, P, Mg, Na, Ca, Zn, Fe, Mn, Co, Cu, Mo and B), (ii) sulfuric acid and (iii) phosphoric acid, the mixture had a pH of 0.8 and was provided at a flow rate of 110 mL/h; and (3) water, provided at a flow rate of 105 mL/h, in an amount sufficient to dilute the glycerol, mineral salts concentrate, sulfuric acid and phosphoric acid to achieve the concentrations shown in Table 1 below. Each of the three components was separately sterilized by autoclave prior to being supplied to the fermenter.

The composition and relative rates of supply of the three components was adjusted independently in order to control the dilution rate (growth rate) of the fermentation and the composition of the fermenter. Preferably, the concentrations of nutrients in the fermenter were as shown in Table 1:

TABLE 1

Concentrations of nutrients in the net feed to the fermenter

| Component | Concentration (g/L) |
|---|---|
| Glycerol | Approximately 80 g/L |
| S | 1.96 |
| K | 1.49 |
| P | 1.02 |
| Mg | 0.200 |
| Na | 0.068 |
| Ca | 0.014 |
| Zn | 0.0026 |
| Fe | 0.00085 |
| Mn | 0.00025 |
| Co | 0.000041 |
| Cu | 0.000043 |
| Mo | 0.000078 |
| B | 0.000021 |

The concentrations listed in Table 1 are suitable concentrations of each component under the present conditions described. It is possible, however, that the concentration of each element in Table 1 can be varied by either increasing or decreasing the concentration of the particular element as necessary.

Prior to inoculation, the fermenter was charged partially with nutrient medium and left overnight to equilibrate both DO and pH probes. The temperature and pH of the fermenter was adjusted to set points (35° C., pH 3.6), by heating and supply of 28% aqueous ammonia to the fermenter as necessary in order to maintain the pH during the fermentation.

The fermenter was inoculated with a 150 mL of seed culture grown overnight in a shaken flask (batch culture), which was in exponential growth phase. The inoculum size of the seed culture was 7.5% (v/v) of the fermenter volume. Continuous fermentation was commenced when the optical density of the cells in the fermenter was ≥10.

The supply of nitrogen to the fermenter was a result of using 28% aqueous ammonia for pH control. The mixture of mineral salts concentrate, sulfuric acid and phosphoric acid was formulated so that the ammonia feed required to maintain constant pH also supplied adequate nitrogen for cell biomass growth with high protein content. The C/N ratio of the media fed to the fermenter was 5.5:1.

The process resulted in a dilution rate (growth rate) of 0.15 $hr^{-1}$ and an average cell density of 55.4 g/L (on a dry basis). The yield of biomass (on a dry basis) per 100 g of glycerol contained within the medium was approximately 70% and the process productivity rate was 8.3 $g.L^{-1}.h^{-1}$.

The fermenter contents were collected continuously using an overflow system into a 20 L carboy, and the collected broth was stored at approximately 4° C. Once full, the 20 L of broth was harvested from the system and centrifuged to afford yeast paste of approximately between 20%-25% w/w solids.

The quality of the yeast paste was assessed initially on the basis of its colour (light tan), aroma (pleasant, non-yeast like), and the crude protein content which was assessed by Kjeldahl analysis to be approximately 55% w/w, on a dry basis (N×6.25).

Example 3

Large Scale Continuous Fermentation of *Candida utilis* in the Presence of Treated Crude Glycerol of Example 1

A 500 L laboratory aerobic fermenter was established with facility for control of pH and temperature and foam, as well as the measurement of dissolved oxygen (DO), the supply of fermentation media and the harvesting of culture in a continuous manner.

The components of the medium included treated crude glycerol of Example 1 (as the sole carbon source), minerals salts concentrate (containing S, K, P, Mg, Na, Ca, Zn, Fe, Mn, Co, Cu, Mo and B), phosphoric acid, sulphuric acid and water. All of these components were pre-mixed in a 5000 L batch in appropriate amounts in order to achieve the concentrations shown in Table 2 below. The combined medium was then pasteurized at 90° C. for 60-90 minutes prior to being fed to the fermenter. The pH of the pasteurized combined medium was approximately 1.8. On a larger scale, the medium components such as the crude glycerol, mineral salts concentrate and water can be fed continuously to a mixer/steriliser and thence to the fermenter to improve energy efficiency and achieve a better control of asepsis.

Prior to inoculation, the fermenter was charged partially with the combined pasteurised medium and sterilised water (100 L of each) and left overnight to equilibrate both DO and pH probes. This initial medium contained 50% of the concentrations of nutrients shown in Table 2. The temperature and pH of the fermenter was adjusted to set points (35° C., pH 3.6), by heating and supply of gaseous ammonia as necessary in order to maintain pH.

TABLE 2

Concentration of nutrients in the net feed to the fermenter

| Component | Concentration (g/L) in fermenter |
|---|---|
| Glycerol | 87 |
| S | 2.31 |
| K | 1.88 |
| P | 1.08 |
| Mg | 0.245 |
| Na | 0.085 |
| Ca | 0.017 |
| Zn | 0.0032 |
| Fe | 0.00104 |
| Mn | 0.00031 |
| Co | 0.000050 |
| Cu | 0.000053 |
| Mo | 0.000096 |
| B | 0.000026 |

The fermentor was inoculated with 20 L of a seed culture having a cell density of 50 g/L collected from a 2 L continuous fermenter (such as described in Example 2). The combined ferment of 220 L was then allowed to ferment aerobically in batch mode for 8 hours. Ammonia (gaseous) was fed to the fermenter as required in order to maintain pH control in the range of 3.60-3.65 during the fermentation. Air was supplied at 1-2 fermenter volumes per minute.

After this time, additional combined pasteurized media was fed to the fermenter at a rate of 30 L/hr in fed-batch mode until the liquid volume reached 300 L. Due to aeration, foam and gas hold-up, the total volume in the fermenter was close to 450 L, although only 300 L of liquid was present. Once the liquid volume reached 300 L, material was then removed from the fermenter at the same rate at which it was fed so that the fermenter was operating in a continuous mode. The overall C/N ratio supplied to the fermentor was 9.3:1.

Within approximately 24 hours, the cell density reached a steady state concentration, and the fermenter was maintained in steady state with minor perturbations for at least 3 days. For a flow rate of 30 L/hr, the Dilution Rate was, therefore, 0.1 $h^{-1}$.

The collected material continuously removed from the fermenter was rapidly cooled to approximately 4° C. and stored for less than 3 days in a 1000 L harvest tank prior to centrifugation, washing and downstream processing. On a larger scale, the batch storage of the yeast harvest can be replaced by continuous centrifugation of the yeast from the fermenter broth as it is collected.

The steady state cell density achieved using this system was 38.2 g/L on a dry basis and the yield of biomass was approximately 44%. The process productivity rate was 3.82 $g.L^{-1}.h^{-1}$.

The quality of the yeast paste was assessed initially on the basis of its colour (light tan), aroma (pleasant, non-yeast like), and the crude protein content was assessed by Kjeldahl analysis to be approximately 58% w/w on a dry basis (N×6.25). The material was further processed by drum drying or conversion into yeast extract. In both cases, the product was judged to have excellent organoleptic qualities.

Example 4

Fed-Batch Fermentation of *Candida utilis* in the Presence of Treated Crude Glycerol A 2 L fermenter equipped with recirculation and aeration system, foam control system, DO measurement system and pH and temperature monitoring and control system, was sterilised by autoclave. The fermenter was then charged with 150 mL of sterilised fermentation medium which included the following three components:

(1) treated crude glycerol (which had been treated in the same manner as described in Example 1, having a concentration of approximately 500 g/L glycerol and a pH of 4.0;

(2) a mixture of (i) mineral salts concentrate (containing S, K, P, Mg, Na, Ca, Zn, Fe, Mn, Co, Cu, Mo and B), (ii) sulfuric acid and (iii) phosphoric acid, and the pH of the mixture was 0.8; and (3) water, in an amount sufficient to dilute the glycerol and the mixture of mineral salts concentrate, sulfuric acid and phosphoric acid in order to achieve the initial concentrations shown in Table 3 below. Each of the three components was separately sterilized by autoclave prior to being supplied to the fermenter.

TABLE 3

Initial concentration of nutrients in the fermenter

| Component | Concentration |
|---|---|
| Glycerol | 100 |
| S | 2.45 |
| K | 1.86 |
| P | 1.28 |
| Mg | 0.250 |
| Na | 0.085 |
| Ca | 0.018 |
| Zn | 0.0033 |
| Fe | 0.0011 |
| Mn | 0.00031 |
| Co | 0.000051 |
| Cu | 0.000054 |
| Mo | 0.000098 |
| B | 0.000026 |

The fermenter was inoculated with 150 mL of a culture of live yeast (prepared by inoculation of flask of 150 mL media with the substantially aseptic washing (2 mL) of a freshly prepared agar slope of yeast culture). The broth was recirculated, aerated and allowed to ferment at a temperature of 35° C. and pH 3.6. Ammonia (28% aqueous) was used to maintain the pH.

After 2 hours, further media was supplied to the batch at a total rate of 27 mL/hr. The composition of this media that was fed was the same as in Table 3. This flow rate was increased every 2 hours, so that the new flow rate was equal to 0.09 times the accumulated volume of the fermenter at the time of adjustment.

After 22 hours from the inoculation, the fermentation was complete (i.e. vessel full). The cell density at this time was measured as 75 g/L (on a dry basis) and the yield was approximately 75%. The process productivity rate was 3.4 $g.L^{-1}.h^{-1}$ and the C/N supplied to the fermenter was 4.2:1. The yeast paste was judged to have excellent organoleptic qualities.

Example 5

Preparation of Yeast Extract and Yeast Cell walls from the *Candida utilis* Grown in the Presence of Treated Crude Glycerol This example illustrates the preparation of a product derived from yeast that has been grown on crude glycerol, in good yield and with no adverse odours or flavours derived from the use of crude glycerol.

A 250 ml conical flask was charged with 68.0 grams (on a wet basis) of crude glycerol-derived yeast paste (obtained in a similar manner as described in Example 2) which contained approximately 25% w/w solids (i.e. 17.0 g, on a dry basis). Water was then added to the paste up to the 100 ml mark. The conical flask was sealed and the mixture was vigorously shaken so as to obtain a homogenous mixture. The pH of the reaction mixture at this stage was between 4.5 and 4.6. The pH of the reaction mixture was adjusted to pH 8.5 using 1.3 mL of 1N NaOH. This reaction mixture was then kept in a shaker water bath which was maintained at 70° C. To the reaction mixture, 0.1 wt % (17 mg/100 ml) of the enzyme Protex 6L™ was added (obtained from Genencor).

The reaction mixture was sampled at 4, 8, 16, 20, 24, 36 and 48 hours. During every sampling, 10 ml of the reaction mixture was taken in a graduated glass centrifuge tube. The sample was centrifuged at 4000 rpm for 5 minutes at a temperature of 5° C. At the end of the centrifugation, all the supernatant obtained was transferred into a graduated glass tube and the volume of the supernatant measured and recorded (approximately 6.5 mL). The supernatant (5 mL)

was transferred onto a pre-weighed watch glass and the watch glass was placed in an oven at 105° C. for approximately 24 hours. From the dry weight % of the supernatant and its volume, the % yield was calculated to be 57%, i.e. 9.7 g of extract (dry basis).

The supernatant from the centrifuged reaction mixture was retained as a soluble yeast extract, and the residue consisted mostly of yeast cell walls (which can be used for further processing to obtain beta-glucan and mannan-rich fractions).

The nitrogen content of the supernatant yeast extract was measured by Kjeldahl analysis (Buchi AG), affording a measure of the crude protein (N×6.25). The free-amino nitrogen content was measured by the Formol titration method (Am J Enol Vitic, 52, 4, 400-401, which is incorporated herein by reference). From these two measurements, the degree of hydrolysis was calculated, as the ratio of free-amino nitrogen to total nitrogen and the results are summarized below. The concentration of glutamate in the yeast extract was measured spectrophotometrically using a commercially available enzymatic test kit (Megazymes Intl) and the results are also summarized below.

Time to complete digestion: approximately 24 hours
Yield: 57%, i.e. 9.7 g of extract on a dry basis from 17 g of yeast paste on a dry basis
Concentration of the yeast extract: approximately 10-13% w/w (on a dry basis) in the supernatant
% Nitrogen content in yeast extract: approximately 8.5-10.0% w/w (on a dry basis)
% FAN at the end of 24 hours: approximately 3.5-5.0% w/w (on a dry basis)
% DH at the end of 24 hours: approximately 45-55%
% Glutamate: approximately 11-12% of the yeast extract (on a dry basis)
Sensory Analysis: Pleasant savory/meaty flavour (2% solution).
: No trace odours or flavours similar to those in the crude glycerol could be detected.

In addition to the above experiment, several other experiments were carried out wherein different proteases were tested in an attempt to optimize the reaction conditions for these particular enzymes. Key parameters such as pH, incubation temperatures and reaction times were varied. A sensory analysis was also carried out on all the yeast extracts that were generated from the optimization experiments summarized below in Table 4:

TABLE 4

Experimental results of pH, temperature and reaction time optimization

| Enzyme | Time | Temperature | pH | % Yield (on a dry basis) | Flavour |
|---|---|---|---|---|---|
| Protex6L | 24 hours | 70° C. | 7.5 | 51.2 | Meaty/Savoury |
| Protex6L | 24 hours | 70° C. | 8.0 | 48.2 | Meaty/Savoury |
| Protex6L | 24 hours | 70° C. | 8.5 | 57.4 | Meaty/Savoury |
| Protex6L | 24 hours | 55° C. | 7.5 | 41.0 | Bitter |
| Protex6L | 24 hours | 55° C. | 8.0 | 43.8 | Bitter |
| Protex6L | 24 hours | 55° C. | 8.5 | 38.6 | Bitter |
| Bromelain | 24 hours | 70° C. | 7.0 | 38.2 | Bitter |
| Bromelain | 24 hours | 70° C. | 7.5 | 40.1 | Bitter |
| Bromelain | 24 hours | 70° C. | 8.0 | 42.1 | Bitter |
| Bromelain | 24 hours | 55° C. | 7.0 | 42.1 | Bitter |
| Bromelain | 24 hours | 55° C. | 7.5 | 41.2 | Bitter |
| Bromelain | 24 hours | 55° C. | 8.0 | 41.9 | Bitter |
| Alcalase 2.4 LFG | 48 hours | 55° C. | 7.0 | 51.1 | Bitter |
| Fungal Protease 60000 | 48 hours | 55° C. | 6.0 | 58.3 | Unpalatable |
| Papain 6000 L | 48 hours | 70° C. | 6.0 | 48.7 | Fishy |
| Validase FP 1000G | 48 hours | 55° C. | 6.5 | 56.1 | Lemony |
| Promod 144P + Promod 192P + Depol 667P | 48 hours | 55° C. | 6.0 | 57.4 | Unacceptable |

During the course of this experimentation, it was found that the digestion of TCG-derived yeast cells by PROTEX 6L™ at 70° C. and pH 8.5 were suitable conditions for producing a yeast extract in 57% yield with an attractive light yellow colour and a meaty flavour.

Example 6

Preparation of Dried Yeast Cell Wall from *Candida utilis* Grown in the Presence of Treated Crude Glycerol Cells of *Candida utilis* were prepared on large scale in accordance with the process described in Example 3. The resulting paste was then used to prepare yeast extract in accordance with Example 5. The residue after removal of the yeast extract solution by centrifugation was re-suspended in an equal volume of water and re-centrifuged. This washing process was repeated a further two times. The resulting residue (containing approximately 20% dry matter) was then re-suspended to a concentration of 10% w/w solids and fed to a steam-heated rotary drum dryer. The feed rate to the dryer was approximately 70-90 ml per minute and was adjusted regularly to match the rotation speed of the dryer and prevent any accumulation of paste on the drum.

The collected dried solid was then subjected to a particle size reduction by grinding in a pestle and mortar, affording a free-flowing powder. This was found to contain 93.3% dry matter, of which approximately 10.5% was analysed as beta-glucan (on a dry basis), according to the method provided by Megazymes Ltd, Ireland.

Example 7

Preparation of Beta-Glucans from Yeast Cell Walls Obtained from *Candida utilis* Grown in the Presence of Treated Crude Glycerol The yeast cell wall (formed as a byproduct from the yeast extract process described in Example 5 above) was found to contain approximately 10.5% beta-glucan (on a dry matter basis). After removal of alpha-glucan (by treatment with an alpha-amylase enzyme) and lipid (by extraction with 2-propanol at reflux for 2 hours), the beta-glucan content was raised to 15%. Extraction with hot sodium citrate buffer (to remove mannoprotein components) was found to raise the beta-glucan content of the residue to 20%. The beta-glucan content was measured using the enzymatic assay kit available from Megazyme International Ireland Ltd.

Example 8

Preparation of Mineralized Yeast Product Derived from *Candida utilis* Grown in the Presence of Treated Crude Glycerol A 2 L fermenter equipped with recirculation and aeration system, foam control system, pH and temperature monitoring and control system and DO measurement system was sterilised by autoclave. The fermenter was charged with 1750 mL of sterile fermentation medium that included the following three components:

1) 250 mL of treated crude glycerol (as the sole carbon source) was prepared according to the method in Example 1 and it contained 650 g/L of glycerol;
2) 0.5 L of a mixture of (i) mineral salts concentrate (containing S, K, P, Mg, Na, Ca, Zn, Fe, Mn, Co, Cu, Mo and B), (ii) nitric acid and (iii) phosphoric acid; and
3) 1 L of water The initial concentration of nutrients in the fermenter was as shown in Table 5 below:

TABLE 5

Initial concentration of nutrients in the fermenter

| Component | Concentration (g/L) in fermenter |
|---|---|
| Glycerol | Approximately 93 |
| N (from nitric acid) | 1.46 |
| S | 0.04 |
| K | 1.38 |
| P | 0.944 |
| Mg | 0.185 |
| Na | 0.063 |
| Ca | 0.013 |
| Zn | 0.0024 |
| Fe | 0.00079 |
| Mn | 0.00023 |
| Co | 0.000038 |
| Cu | 0.000040 |
| Mo | 0.000072 |
| B | 0.000019 |

The pH was corrected to 3.6 using aqueous ammonia, then the contents were inoculated with 200 mL of a pure seed culture (prepared by overnight batch fermentation in a shaken flask).

The system was allowed to ferment in batch mode overnight at 35° C., or until an optical density at 700 nm of 10 was achieved. The system was then switched on to continuous mode, in which treated crude glycerol (prepared in accordance with Example 1, 65% w/v) was fed at 26 mL/hr. The mixture of mineral salts concentrate, nitric acid and phosphoric acid was fed at 69 mL/hr, and water was supplied at 56 mL/hr, in order to maintain a feed composition as shown in Table 6:

TABLE 6

Concentration of nutrients in the net feed to the fermenter

| Component | Concentration (g/L) in fermenter |
|---|---|
| Glycerol | Approximately 110 |
| N (from nitric acid) | 5.10 |
| S | 0.06 |
| K | 1.99 |
| P | 1.32 |
| Mg | 0.267 |
| Na | 0.091 |
| Ca | 0.019 |
| Zn | 0.0035 |
| Fe | 0.00114 |
| Mn | 0.00033 |
| Co | 0.000055 |
| Cu | 0.000058 |
| Mo | 0.000104 |
| B | 0.000027 |

The dilution rate was 0.1 $h^{-1}$, after including agents for control of pH (aqueous ammonia) and foam (such as Dow-Corning Antifoam 1520US™).

During the fermentation, the pH was maintained between 3.6 and 3.7 by automatic addition of aqueous ammonia as required. The temperature was allowed to rise to 35.0° C., and then maintained at this temperature by supply of cooling water as required.

When the cell density in the fermenter had achieved a steady state (or more than 40 g of dry biomass per litre), the mixture of mineral salts concentrate, nitric acid and phosphoric acid was replaced by a modified mineral salts mixture which was identical in composition to the feed composition shown in Table 6, with the exception that sodium selenite, at a concentration of 0.11 g/L, was also present in the feed composition.

After allowing the fermenter to achieve a new steady state equilibrium whilst being fed the modified mineral salts mixture (which occurred within approximately 24 to 48 hours), a second modified mineral salts mixture was then used, in which the concentration of sodium selenite was increased such that the selenium concentration in the feed composition was 0.22 g/L. Another period of equilibration was allowed, after which a third modified mineral salts mixture was used in which the concentration of sodium selenite was increased such that the selenium concentration in the feed composition was 0.33 g/L.

In this manner, the concentration of selenium in the fermenter feed (at steady state) was increased. The increase was continued until the point where the level of selenium became toxic to the yeast growth, as observed by a decrease in cell density to less than 30 g/L on a dry basis. This corresponded to a yield of biomass from glycerol of 35%. Fermentation was stopped at the point at which the cell density decreased to approximately 30 g/L.

The productivity of the continuous fermentation at the point at which it was stopped was 3 $g.L^{-1}h^{-1}$. The C/N ratio in the feed supplied to the fermenter was 10.6:1.

The overflow from the fermenter was collected and stored at 4° C. The harvest was periodically removed, concentrated by centrifugation and the resulting yeast paste was drum dried to >90% wt/wt solids content. The selenium content of the yeast was measured by Atomic Absorption Spectroscopy and the results are summarized in Table 7. The organoleptic properties of the dried yeast were judged to be acceptable and free from taints derived from the crude glycerol feedstock.

TABLE 7

Selenium content of mineralized yeast product

| Sodium Selenite concentration in feed to fermenter, g/L | Cell Density, g/L | Selenium concentration in Yeast, ppm |
| --- | --- | --- |
| 0 | 50 | 0 |
| 0.11 | 41 | 500 |
| 0.22 | 42 | 1820 |
| 0.33 | 35 | 2580 |

It is to be understood that the present invention has been described by way of example only and that modifications and/or alterations thereto, which would be apparent to a person skilled in the art based upon the disclosure herein, are also considered to fall within the scope and spirit of the invention, as defined in the appended claims.

The claims defining the invention are as follows:

1. A process for preparing a nutritional, therapeutic or organoleptic product comprising:
   (a) growing non-recombinant yeast, under aerobic conditions, in the presence of a medium comprising one or more carbon sources, one of which is crude glycerol containing approximately from 15% to approximately 95% wt/wt glycerol and the concentration of glycerol in the medium is approximately from 50.0 to approximately 500.0 g/L, and one or more sources of nitrogen to produce a yeast product; wherein the carbon to nitrogen ratio of the medium is less 90:1; and
   (b) processing the yeast product to obtain the nutritional, therapeutic or organoleptic product,
wherein the growth of the yeast exhibits a process productivity rate of greater than or equal to 0.85 gram of yeast biomass on a dry basis per liter of medium per hour ($g.L^{-1}.h^{-1}$).

2. The process as claimed in claim 1, wherein the crude glycerol undergoes one or more treatments to remove one or more impurities before being added to the medium.

3. The process as claimed in claim 1, wherein the crude glycerol is the sole source of carbon and the crude glycerol contains approximately from 20% to approximately 95% wt/wt glycerol.

4. The process as claimed in claim 1, wherein the yeast is grown in a continuous mode.

5. The process as claimed in claim 1, wherein the concentration of glycerol in the medium is approximately from 70.0 to approximately 200.0 g/L.

6. The process as claimed in claim 1, wherein the yeast is *Candida utilis, Candida curvata, Candida hispaniensis, Candida bentonensis, Kluyveromyces marxianus, Saccharomyces bayanus* or a combination thereof.

7. The process as claimed in claim 1, wherein the yeast is *Candida utilis*.

8. The process as claimed in claim 1, wherein the cell density is approximately from 5.0 g/L to greater than or equal to 150.0 g/L on a dry basis.

9. The process as claimed in claim 1, wherein the growth of the yeast exhibits a process productivity rate of greater than or equal to 1.00 gram of yeast biomass on a dry basis per liter of medium per hour ($g.L^{-1}.h^{-1}$).

10. The process of claim 1, wherein the medium further comprises one or more elements selected from the group consisting of selenium, chromium, molybdenum, germanium, zinc, iron, copper, magnesium, manganese and iodine to produce a mineralized yeast product with an enhanced level of the one or more selected elements; and the mineralized yeast product is processed to obtain the nutritional, therapeutic or organoleptic product.

11. The process as claimed in claim 10, wherein the enhanced level is from approximately 100 to approximately 50000 ppm of each enhanced element on a dry basis.

12. The process as claimed in claim 10, wherein the element is selenium.

13. The process as claimed in claim 10, wherein the crude glycerol undergoes one or more treatments to remove one or more impurities before being added to the medium.

14. The process as claimed in claim 10, wherein the crude glycerol is the sole carbon source and the crude glycerol contains approximately from 20% to approximately 95% wt/wt glycerol.

15. The process as claimed in claim 10, wherein the yeast is grown in a continuous mode.

16. The process as claimed in claim 10, wherein the concentration of glycerol in the medium is approximately from 70.0 to approximately 500.0 g/L.

17. The process as claimed in claim 10, wherein the yeast is *Candida utilis, Candida curvata, Candida hispaniensis, Candida bentonensis, Kluyveromyces marxianus, Saccharomyces bayanus* or a combination thereof.

18. The process as claimed in claim 10, wherein the yeast is *Candida utilis*.

19. The process as claimed in claim 10, wherein the cell density is approximately from 5.0 g/L to greater than or equal to 150.0 g/L on a dry basis.

20. The process as claimed in claim 10, wherein the growth of the yeast exhibits a process productivity rate of greater than or equal to 1.00 gram of yeast biomass on a dry basis per liter of medium per hour ($g.L^{-1}.h^{-1}$)

21. The process as claimed in claim 10, wherein the element is zinc.

22. The process as claimed in claim 1, wherein the carbon to nitrogen ratio is less than or equal to 80:1.

23. The process as claimed in claim 1, wherein the concentration of glycerol in the medium is approximately from 50.0 to approximately 200.0 g/L.

* * * * *

UNITED STATES PATENT AND TRADEMARK OFFICE
CERTIFICATE OF CORRECTION

PATENT NO. : 8,802,408 B2  
APPLICATION NO. : 12/863152  
DATED : August 12, 2014  
INVENTOR(S) : Fieldhouse et al.

Page 1 of 1

It is certified that error appears in the above-identified patent and that said Letters Patent is hereby corrected as shown below:

In the Specification

Column 1, lines 25-26: "(see http://www.biodiesel.org/pdf files/fuelfactsheets/production capacity.pdf)."

should read

-- (see http://www.biodiesel.org/pdf_files/fuelfactsheets/production_capacity.pdf). --.

Column 4, line 4: "treatment" should read -- treatments --.

Column 5, line 4: "*Kluyveromyces mandanus*" should read -- *Kluyveromyces marxianus* --.

Signed and Sealed this  
Twenty-sixth Day of May, 2015

Michelle K. Lee  
*Director of the United States Patent and Trademark Office*